(12) United States Patent
Boyd

(10) Patent No.: US 7,942,799 B1
(45) Date of Patent: May 17, 2011

(54) KNEE JOINT FLEXURE PROGRESSION METER

(76) Inventor: Gary G. Boyd, Retsof, NY (US)

( * ) Notice: Subject to any disclaimer, the term of this patent is extended or adjusted under 35 U.S.C. 154(b) by 0 days.

(21) Appl. No.: 12/577,438

(22) Filed: Oct. 12, 2009

(51) Int. Cl.
A63B 23/00 (2006.01)
B43L 7/10 (2006.01)
B26B 29/06 (2006.01)

(52) U.S. Cl. .............................. 482/148; 33/471; 33/473
(58) Field of Classification Search .................. 482/148; 33/511–512, 515, 417–419, 470–473, 455, 33/468
See application file for complete search history.

(56) References Cited

U.S. PATENT DOCUMENTS

| | | | | |
|---|---|---|---|---|
| 1,346,409 A * | 7/1920 | Lucas | | 33/473 |
| 1,632,267 A * | 6/1927 | Beem | | 33/473 |
| 1,635,874 A * | 7/1927 | Wynkoop | | 33/473 |
| 4,394,801 A * | 7/1983 | Thibodeaux | | 33/496 |
| 4,813,149 A * | 3/1989 | Herkimer | | 33/462 |
| 4,916,822 A * | 4/1990 | Johnson | | 33/458 |
| 4,939,849 A * | 7/1990 | Johnson | | 33/811 |
| 5,205,045 A * | 4/1993 | Liu | | 33/468 |
| 5,461,794 A * | 10/1995 | Huang | | 33/470 |
| 5,983,509 A * | 11/1999 | Gosselin et al. | | 33/1 SD |
| 6,049,990 A * | 4/2000 | Holland | | 33/464 |
| 6,105,269 A * | 8/2000 | Kondrat | | 33/512 |
| 6,260,283 B1 * | 7/2001 | Abernathy et al. | | 33/419 |
| 6,470,591 B2 * | 10/2002 | Rutkowski | | 33/832 |
| 6,694,633 B1 * | 2/2004 | Nyquist | | 33/452 |
| 6,829,837 B2 * | 12/2004 | Williams | | 33/473 |
| 7,047,655 B2 * | 5/2006 | Larsson | | 33/471 |
| 7,082,692 B2 * | 8/2006 | Shapiro | | 33/473 |
| 7,188,427 B2 * | 3/2007 | Johnson | | 33/471 |
| 7,254,898 B1 * | 8/2007 | Armstrong | | 33/464 |
| 7,549,231 B1 * | 6/2009 | Neubauer | | 33/464 |
| 7,739,806 B1 * | 6/2010 | Pater | | 33/417 |
| 7,797,842 B2 * | 9/2010 | Fernandes | | 33/27.03 |
| 2002/0148127 A1 * | 10/2002 | Dana et al. | | 33/456 |
| 2003/0171196 A1 | 9/2003 | Cunningham | | |

* cited by examiner

Primary Examiner — Steve R Crow
(74) Attorney, Agent, or Firm — Mark Levy; Hinman, Howard & Kattell, LLP

(57) ABSTRACT

A knee joint flexure progression meter and system. The knee joint flexure meter has an elongated progression meter bar with a major axis, an upper surface, a lower surface having a longitudinal recess therein, and a plurality of spaced apart indicia disposed on the upper surface thereof. A crossbar is disposed perpendicularly to the progression meter bar major axis. The crossbar is both adjustable and removable with respect to the progression meter bar. The crossbar is dimensioned smaller than the recess in the progression meter bar, so that the crossbar can be contained within the recess. A mechanism is provided for containing the crossbar within the progression meter bar for transportation or temporary storage.

3 Claims, 4 Drawing Sheets

KNEE JOINT FLEXURE PROGRESSION METER

FIELD OF THE INVENTION

The invention pertains to metering devices that indicate knee joint flexibility and, more particularly, to a device used to monitor the progressive increase of flexibility of a knee joint after surgery or the like.

BACKGROUND OF THE INVENTION

Knee surgery involves cutting, stretching, displacement, and/or other impairment of flesh, bone, muscle, ligament, and/or tendon in and near the knee joint. Full recovery from such surgery, when possible, generally requires exercise to regain the tone and full use of these biological articles.

Following surgery, the knee joint is usually swollen and stiff. In time, and with proper and regular exercise, swelling and stiffness can be reduced or even eliminated, and flexure (i.e., the ability to extend and retract the lower leg relative to the upper leg) can be restored to the knee. A patient who sees a positive effect or progress due to his or her exercise routine is more likely to continue to exercise. Any of a number of exercise regimens can be used to accomplish the goal of improved or full knee flexure, but such exercise regimens form no part of the present invention.

United States Published Patent Application No. 2003/0171196, published Sep. 11, 2003 on application of James J. Cunningham for POST OPERATIVE KNEE FLEXER, purportedly discloses an apparatus for allowing a patient, who is recovering from knee surgery, to adjust his or her lower leg. No description of a metering device is found in the reference, although a protractor to represent relative positioning between two structural elements is shown attached to the machine.

It would be advantageous to provide a device for measuring the amount of flexure of a knee joint after surgery thereon.

It would also be advantageous to provide a non-intrusive progressive metering device that would accurately indicate the degree of flexure of a knee joint as a function of a lower leg attached thereto.

It would further be advantageous to provide a portable measuring or metering device for indicating the degree of flexure of a knee joint.

It would also be advantageous to provide a progressive metering device that could be stored or transported easily by the user thereof.

It would also be advantageous to provide a self-positioning progressive metering device that can be disposed proximate the legs of any conventional chair.

SUMMARY OF THE INVENTION

In accordance with the present invention, there is provided a knee joint flexure progression meter and system. The knee joint flexure meter has an elongated progression meter bar with a major axis, an upper surface, a lower surface having a longitudinal recess therein, and a plurality of spaced apart indicia disposed on the upper surface thereof. A crossbar is disposed perpendicularly to the progression meter bar major axis. The crossbar is both adjustable and removable with respect to the progression meter bar. The crossbar is dimensioned smaller than the recess in the progression meter bar, so that the crossbar can be contained within the recess. A mechanism is provided for containing the crossbar within the progression meter bar for transportation or temporary storage.

The metering device of this invention is for use on a regular (e.g., daily) basis to make time-after-time comparisons of knee joint flexure, to thereby monitor its progress.

The system can further include a seat for the user permitting forward and rearward leg movement with knee flexure, the seat front legs also serving as abutments against which to abut the ends of the crossbar, thus establishing its reference position.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENT

The invention is a knee joint flexure progression meter and system. The knee joint flexure meter has an elongated progression meter bar with a major axis, an upper surface, a lower surface having a longitudinal recess therein, and a plurality of spaced apart indicia disposed on the upper surface thereof. A crossbar is disposed perpendicularly to the progression meter bar major axis. The crossbar is both adjustable and removable with respect to the progression meter bar.

Figure 1:
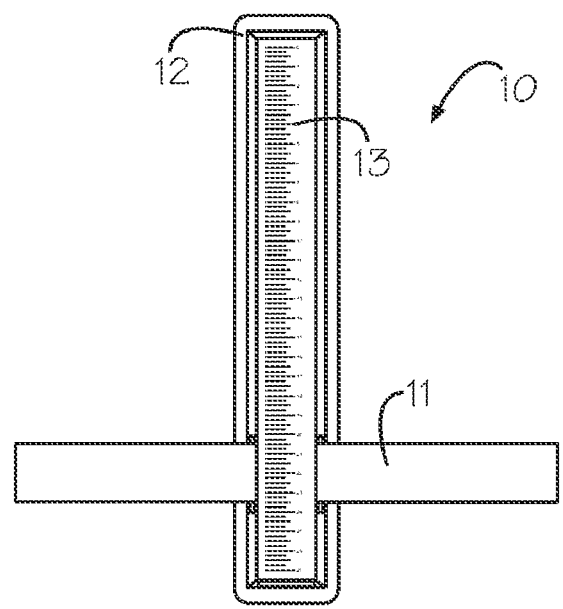
FIG. 1 is a plan view of the knee joint flexure progression meter of this invention in its deployed state.

Referring now to FIG. 1, there is shown the progression meter or flexure meter 10, in accordance with the invention. A crossbar 11 is provided and a progression meter bar 12 extends forward and rearward of the crossbar 11 and perpendicular thereto. The progression meter bar 12 includes indicia 13 along its length to indicate inches, centimeters, or other units of length, which can be arbitrary, graphical, or the like. It should be understood that other symbols or markings may be used to indicate progress made by the patient in the course of his or her exercises.

Figure 2:
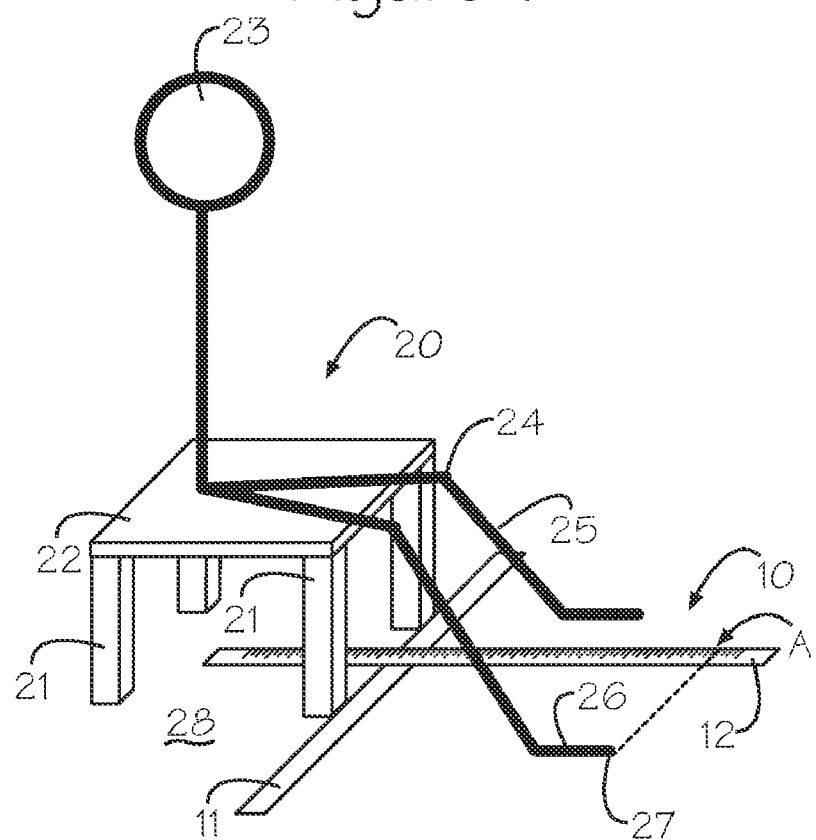
FIGS. 2 and 3 are illustrations of the flexure meter in operation.

FIG. 2 represents a support 20 such as a chair or coffee table with legs 21 and a top surface or seat 22 on which a sitting person (the "user") 23 is positioned. The user's knee joint 24, lower leg 25, and foot 26 are positioned as shown. The numeral 27 represents the end of the foot (i.e., the tip of the great toe).

The flexure meter 10 is positioned on the floor 28 with its crossbar 11 abutting the front table legs 21. The table legs 21 provide fixed abutments and a reference line against which to repeatedly position the meter 10 for use time after time. The major axis of meter bar 12 extends forward and backward, perpendicularly, from the axis of crossbar 11.

In FIG. 2, the user's lower leg 25 is flexed to a certain extent as permitted by user's knee condition. The position (indicated by arrow A) of the great toe 27 relative to indicia 13 on the meter bar 12 provides a reference against which to compare position readings time after time as knee exercises proceed.

Figure 3:
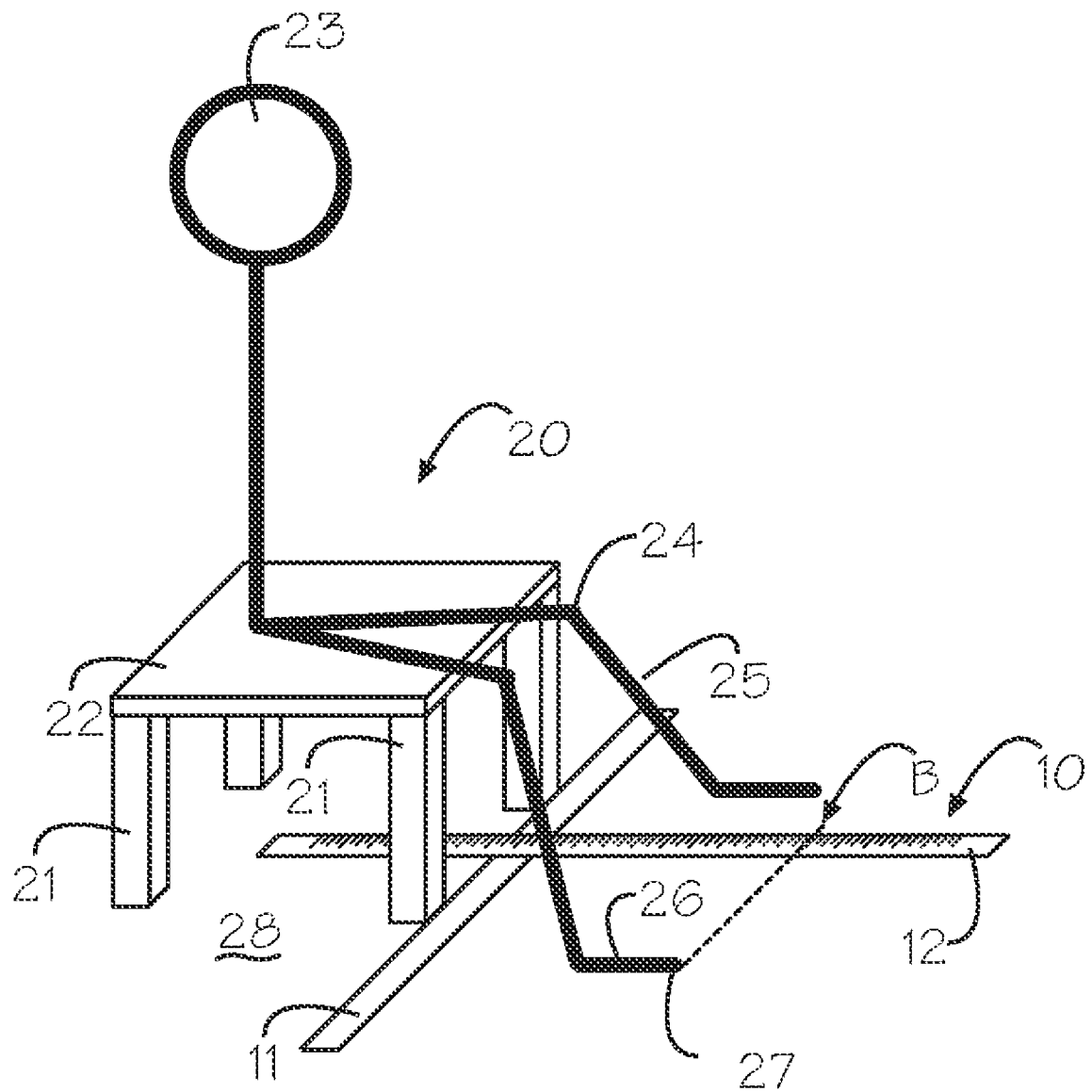

FIG. 3 is similar to FIG. 2, but the knee 24 is flexed to a greater extent, as indicated by the position (arrow B) of the user's toe 27 relative to the meter bar 12.

Periodic comparison of positions of a toe 27 relative to the meter bar 12 is a simple and easy way to monitor the progress of the user's exercises and knee flexure.

Figure 4:
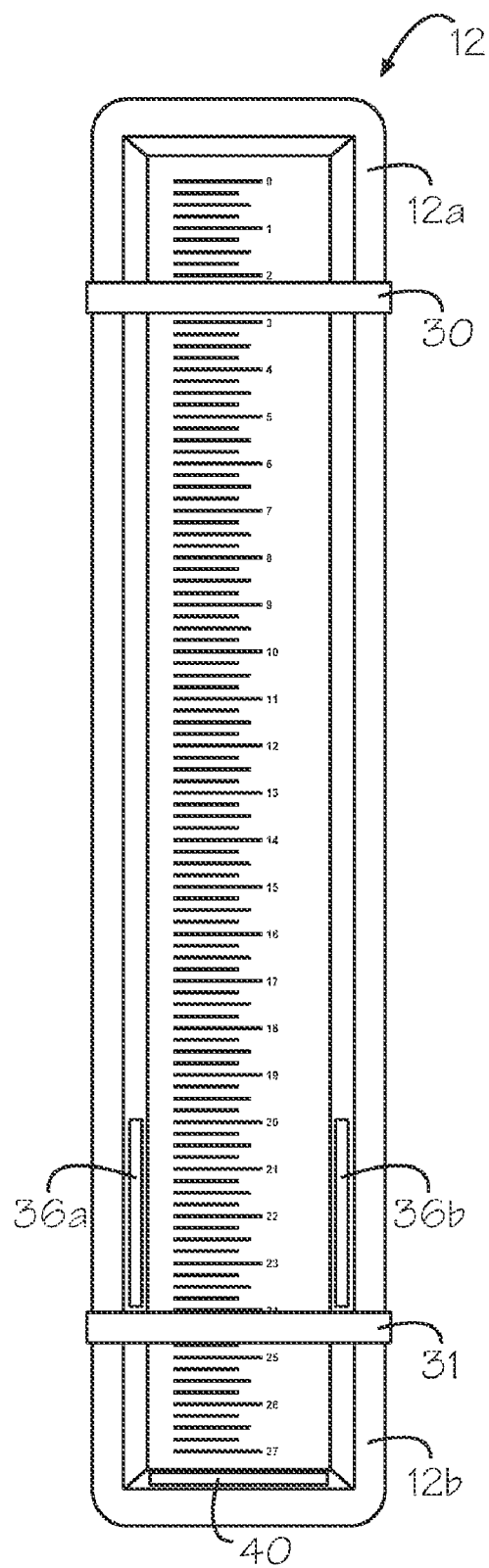
FIG. 4 is an enlarged plan view of the upper surface of the progression meter bar with indicia thereon.

Referring now to FIG. 4, the meter bar 12 is laterally movable or adjustable along the crossbar 11 as desired, in a manner well known by those skilled in the art and further described hereinbelow, for use with the right or left leg 25 of user 23. In FIGS. 2 and 3, the meter bar 12 is in a rightward position on the crossbar 11, for use with the right leg 25 of user 23.

Removably positioned on meter bar 12 are two elastic elements or rubber bands 30, 31, whose function is described hereinbelow. Other elements, not shown, can also be used to accomplish the purpose of the elastic elements 30, 31, including, but not limited to, clamps, hook and loop fasteners, and reusable adhesive tape.

Figure 5:
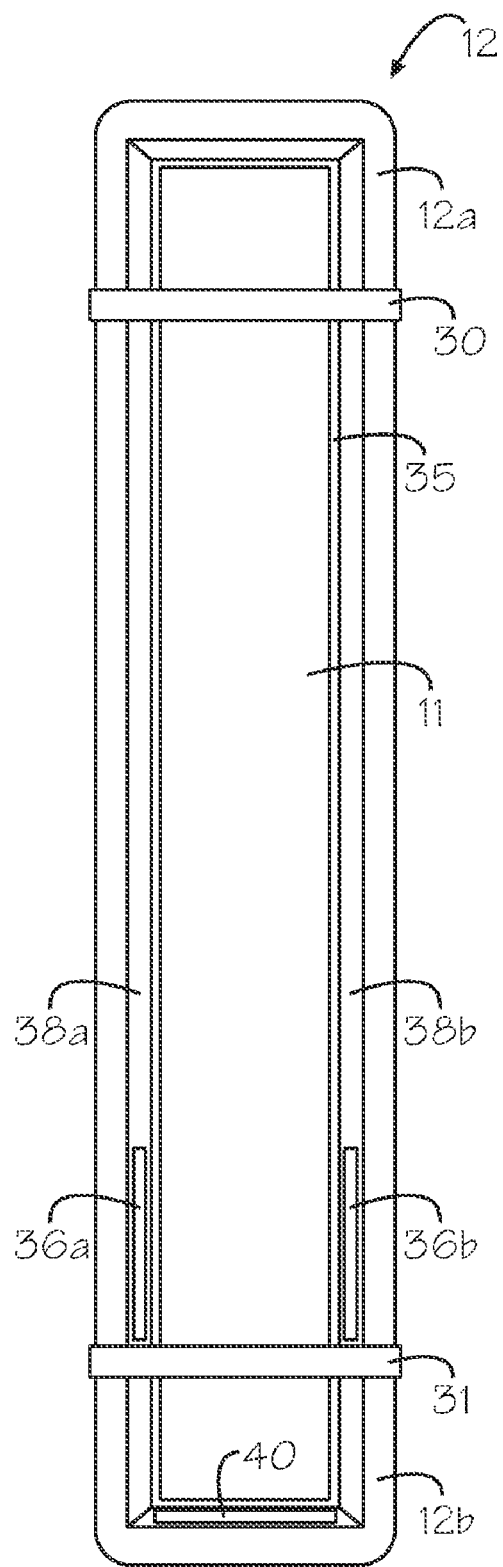
FIG. 5 is a plan view of the rear surface of the progression meter bar showing a longitudinal recess therein.

Referring now also to FIG. 5, there is shown a plan view of the lower surface of meter bar 12. A longitudinal recess 35 extends from the upper boundary 12a to the lower boundary 12b of meter bar 12. The width of longitudinal recess 25 is slightly greater than the width of cross bar 11. Two meter bar slots 36a, 36b are symmetrically formed in the side walls 38a, 38b, respectively of meter bar 12. Each meter bar slot 36a, 36b is slightly longer than the width of cross bar 11. Cross bar 11, therefore, can be inserted in slots 36a, 36b for relative movement of meter bar 12 to accommodate measurement of the left knee flexure or right knee flexure of user 23.

An additional slot 40 is formed at the lower boundary 12b of meter bar 12. Slot 40 is slightly wider than the width of crossbar 11 to accommodate a slight insertion of one end of crossbar 11 in longitudinal recess 35 for transportation or temporary storage of flexure meter 10. To secure crossbar 11 in longitudinal recess 35, elastic elements 30, 31 are positioned as shown. It should be understood, however, that a single elastic element or other suitable clamping means, as are well known to those of skill in the art, may be used to similar effect.

Terms indicative of orientation are not intended as limitations but as description with reference to the drawings. Described structure retains its character whether oriented as shown or otherwise. Any detail as to materials, quantities, dimensions, and the like is intended as illustrative.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A knee joint flexure progression meter, comprising:
   a) an elongated progression meter bar having a major axis, an upper surface, a lower surface having a slot and a longitudinal recess therein and an elastomeric member attached thereto, and a plurality of spaced apart indicia disposed on said upper surface thereof;
   b) a crossbar disposed perpendicularly to said progression meter bar major axis, said crossbar being adjustable and slidably removable with respect to said progression meter bar in said slot, said crossbar having dimensions smaller than the respective dimensions of said progression meter bar lower surface longitudinal recess, said crossbar extending completely through and across said meter bar for placement in a repeatable reference position relative to a user, thereby providing a reference line to observe positions of a user's foot along said meter bar as an indicator of the degree of said user's knee flexure; and
   c) at least one means for containing said progression meter bar and said crossbar disposed completely within said longitudinal recess for transportation or temporary storage, whereby said crossbar is retained in said longitudinal recess by said elastomeric member.

2. The knee joint flexure progression meter in accordance with claim 1, wherein said elastomeric member comprises a rubber band.

3. The knee joint flexure progression meter in accordance with claim 1, wherein said indicia comprises at least one of the group: inches, centimeters, and arbitrary units of measure.

* * * * *